United States Patent [19]  
Eckberg

[11] Patent Number: 5,070,118  
[45] Date of Patent: Dec. 3, 1991

[54] RADIATION-SELF-SENSITIZED SILICONE POLYMERS

[75] Inventor: Richard P. Eckberg, Saratoga, N.Y.

[73] Assignee: General Electric Company, Waterford, N.Y.

[21] Appl. No.: 643,312

[22] Filed: Jan. 22, 1991

Related U.S. Application Data

[62] Division of Ser. No. 170,952, Mar. 21, 1988, Pat. No. 4,988,743.

[51] Int. Cl.$^5$ .................... C08G 77/18; C08L 83/06; C08F 283/12
[52] U.S. Cl. .................................. 522/99; 522/904; 522/148; 525/476; 525/477
[58] Field of Search ............... 522/6, 99, 904, 148; 525/476, 477

[56] References Cited

U.S. PATENT DOCUMENTS

| | | | |
|---|---|---|---|
| 4,477,326 | 10/1984 | Lin | 528/24 |
| 4,608,270 | 8/1986 | Varaprath | 528/26 |
| 4,640,967 | 2/1987 | Eckberg | 528/26 |

*Primary Examiner*—Marion E. McCamish  
*Assistant Examiner*—Susan Berman

[57] ABSTRACT

Polysiloxane is produced containing both acrylic or methacrylic and benzoyl functions which is self-sensitized to UV radiation.

13 Claims, No Drawings

RADIATION-SELF-SENSITIZED SILICONE POLYMERS

This application is a division of application Ser. No. 07/170,952, filed Mar. 21, 1988, now U.S. Pat. No. 4,988,743, issued Jan. 29, 1991.

The present invention relates to UV curable acrylic or methacrylic functional polysiloxanes. More particularly, the present invention relates to acrylic or methacrylic functional polysiloxanes self-sensitized to UV radiation.

BACKGROUND OF THE INVENTION

UV-curable silicone compositions are well represented in the patent literature, and are assuming an increasingly significant share of various silicone coating applications. Such materials are curable by crosslinking reactions between radiation-sensitive functional groups such as acrylic or methacrylic functions attached to silicon atoms in the silicone polymer structure. However, silicones containing radiation-crosslinkable functional groups are not photo-curable unless a photosensitizer or photoinitiator is present in sufficient concentration to be effective.

A long-time problem for practitioners of this art has been the poor solubility of photosensitizers such as benzophenone, diethanolamine, and the like, in organofunctional dimethylsilicone polymers. One approach to this issue has been to produce silicone-functional photoinitiators which are designed to be miscible with silicone fluids.

Shirahata U.S. Pat. No. 4,391,963, teaches the synthesis of silicone-functional benzophenones. These materials are prepared by converting a hydroxybenzophenone to an allyloxy benzophenone, then adding the unsaturated benzophenone derivative to an SiH containing polysiloxane via platinum-catalyzed addition. This scheme is complex and requires conversion of a hydroxybenzophenone (or hydroxyacetophenone) to another intermediate, followed by a hydrosilation reaction. Further, there is a problem that the hydrosilation reaction prevents the simultaneous substitution to the polysiloxane of unsaturated hydrocarbon functions as such functions will be consumed in the reaction. There are other such examples which can be culled from prior art.

It is an object of the present invention to produce a silicone polymer which is self-sensitized to UV radiation.

It is another object of the present invention to produce a polymer having both radiation sensitive acrylic or methacrylic functional and photosensitizing organo-functionality.

It is yet another object to produce such a polymer via one-pot processing by means of well known synthesis techniques.

It is still another object to produce such a polymer without need for hydrosilation reactions.

SUMMARY OF THE INVENTION

There is provided by the present invention a radiation curable silicone polymer comprising:

(a) acrylic or methacrylic functional units in sufficient number to crosslink and cure the polymer of the formula:

$$R_aR_b^1SiO_{(4-a-b)/2} \tag{1}$$

wherein R is hydrogen, or a $C_{(1-8)}$ substituted or unsubstituted hydrocarbon, $R^1$ is a substituted or unsubstituted acrylic or methacrylic functional hydrocarbon of from 3 to about 20 carbon atoms; a is 0, 1 or 2; b is 1, 2 or 3; and a+b is 1, 2 or 3; and (b) benzoyl functional units in sufficient number to promote cure with exposure to ultraviolet radiation of the formula:

$$R_cR_d^2SiO_{(4-c-d)/2} \tag{2}$$

wherein R is given above, $R^2$ is a substituted or unsubstituted benzoyl functional hydrocarbon of from 7 to about 20 carbon atoms; c is 0, 1 or 2; d is 1, 2 or 3; and c+d is 1, 2 or 3. There is also provided a method to produce such a polymer.

DETAILED DESCRIPTION OF THE INVENTION

The radiation curable silicone polymer herein has units of formula (1) and units of formula (2) generally combined with siloxane units of the formula $$R_eSiO_{(4-e)/2} \tag{3}$$

wherein R is hydrogen or a $C_{(1-8)}$ substituted or unsubstituted hydrocarbon and e is 0, 1, 2 or 3. The nature of the various units can be altered to render the silicone polymer herein as either a fluid, gum or resin. Moreover, the relative proportions of the various units can be controlled to determine sensitivity to UV light or crosslink density.

As stated, the nature of the units controls the nature of the silicone polymer. A fluid or gum is substantially linear and might contain units such as:

$R_3SiO_{\frac{1}{2}}$ units, $RR^1SiO_{2/2}$ units,
$RR^2SiO_{2/2}$ units and $R_2SiO_{2/2}$ units or
$R_2R^1SiO_{\frac{1}{2}}$ units, $RR^2SiO_{2/2}$ units,
$RSiO_{3/2}$ units, and $R_2SiO_{2/2}$ units.

A resin might contain units such as:

$RSiO_{3/2}$ units, $R^1SiO_{3/2}$ units and $R^2SiO_{3/2}$ units;
$R_3SiO_{\frac{1}{2}}$ units, $R^1RSiO_{2/2}$,
$R^2RSiO_{2/2}$ units, $R_2SiO_{2/2}$ units, and $SiO_{4/2}$ units;
or $R_2R^1SiO_{\frac{1}{2}}$ units, $RR^2SiO_{2/2}$ units,
$R_2SiO_{2/2}$ units and $SiO_{4/2}$ units.

The relative proportions of the various units should be calculated to achieve the purpose for which the unit is present. For example, the purpose of units for formula (1) is to provide reactive or crosslink sites. Thus, there should be sufficient of these units to provide the desired crosslinking. Generally this will require that units of formula (1) constitute from about 0.1% to about 10% by number of all silicone units in the polymer. Likewise, the purpose of units of formula (2) is to promote the cure of the polymer with exposure to UV light. Thus there should be sufficient of these units to achieve this goal. Generally this will require that units of formula (2) constitute from 0.1% to about 15% by number of all silicone units in the polymer.

Preferred silicone polymers herein are linear and have a viscosity ranging from about 10 to 500,000 centipoise. Such polymers are conveniently employed in coating applications where UV light is commonly employed as the method of cure.

R above is defined as a hydrogen or $C_{(1-8)}$ substituted or unsubstituted hydrocarbon. Among the radicals included within R are alkyl such as methyl, ethyl and propyl; cycloalkyl such as cyclopentyl, cyclohexyl and cycloheptyl; aryl such as phenyl, naphthyl, tolyl and xylyl; aralkyl such as phenylethyl and phenylpropyl; substituted radicals of any of the foregoing, for example halogen substituted and cyanoalkyl substituted; and alkenyl, such as vinyl or allyl. Preferably R is hydrogen or a $C_{(1-8)}$ alkyl or aryl.

$R^1$ is described above as a substituted or unsubstituted acrylic or methacrylic functional hydrocarbon of from 3 to about 20 carbon atoms. Essentially herein $R^1$ contains a linkage resulting from a non-free radical reaction involving the carbonyl of acrylic or methacrylic acid. Such linkages include an amide linkage or an ester linkage. The amide linkage might result from a reaction between a primary amine and an acid chloride or acid ester. The ester linkage might result from a reaction between epoxy or hydroxy and carboxy.

The exact nature of $R^1$ might be better understood by referring to the method to produce the polymer below. Otherwise, $R^1$ includes functional groups represented by the formula:

$$-R^3 - Q -(- C{=}O -)- CR^4{=}CH_2 \quad (4)$$

where $R^3$ is a $C_{(1-15)}$ substituted or unsubstituted hydrocarbon, Q is — O —, —NH— or —(C=O)NH— and $R^4$ is methyl or hydrogen.

$R^2$ is described above as a substituted or unsubstituted benzoyl functional hydrocarbon of from 7 to about 20 carbon atoms. $R^2$ contains a linkage resulting from a non-free radical reaction involving the carbonyl of benzoic acid or derivative. Again, such linkages include an amide linkage or an ester linkage. The amide linkage might result from a reaction between a primary amine and an acid chloride or acid ester. The ester linkage might result from a reaction between hydroxy or epoxy and a carboxylate.

The nature of $R^2$ might be better understood by referring to the method to produce the polymer below. Otherwise $R^2$ includes functional groups represented by the formula:

$$- R^5 - Q - (C{=}O) (R_f^6 C_6H_{5-f}) \quad (5)$$

where $R^5$ is a $C_{(1-15)}$ substituted or unsubstituted hydrocarbon, Q is given above, and $R^6$ is a hydrogen atom, a halogen atom, a monovalent hydrocarbon group of from 1 to 10 carbon atoms, an alkoxy group, a thioalkoxy group, an amino group, or a dialkylamino group.

$R^3$ and $R^5$ might independently be:
— $CH_2CH_2CH_2NH$—, —$CH_2CH_2CH_2 — O$ —,
— $CH_2CH_2$ etc. Preferably $R^1$ and $R^2$ contain the same linkage and most preferably $R^3$ and $R^5$ are the same radical.

The radiation curable silicone polymer herein is produced by any of several methods which have in common a non-free radical reaction involving a carbonyl. According to the invention herein, a silicone base polysiloxane having functional groups reactive with acid chlorides or carboxylic acids or esters are reacted in the absence of UV radiation with acrylic or methacrylic acid or derivative and benzoic acid or derivative. The polymer is recovered by simply removing by-products.

Silicone base polymers with suitable functional groups include epoxy functional silicone polymers, amine functional silicone polymers, hydroxy functional silicone polymers, etc. Such polymers are well known in the art and are increasingly available commercially.

Suitable epoxy functional base silicone polymers may have aliphatic or cycloaliphatic epoxy functions and are generally produced by reacting an unsaturated epoxy group with a silicone hydride in the presence of a platinum catalyst. A preferred epoxy functional base silicone polymer has units of the formula:

$$R_g G_h SiO_{(4-g-h)/2} \quad (6)$$

where R is given above, G is epoxy functional, substituted or unsubstituted hydrocarbon of from 3 to about 15 carbon atoms, g is 0, 1 or 2; h is 1, 2 or 3; and g+h is 1, 2 or 3. Preferably G is cycloaliphatic epoxy functional, especially cyclohexyl epoxy functional. There should be a sufficient number of these units to provide reactive sites for the required acrylic or methacrylic units and to provide reactive sites for the required benzoyl functions. Production of suitable epoxy functional base silicones are taught in U.S. Pat. Nos. 4,640,967; 4,576,999; and 4,585,699, hereby incorporated by reference.

Suitable catalysts to promote the reaction with the base epoxy functional organopolysiloxane include tetraalkylureas and tetraalkylguanidines. Particularly effective are 1,1',3,3'-tetramethylurea and 1,1',3,3'-tetramethylguanidine. The amount is not critical and can range from as little as 0.01% by weight to 5.0% by weight or more based on the bulk reaction mass. Preferably the amount ranges from 0.1% to 2.0% by weight. The quantity of catalyst which is most effective for performing the epoxy/carboxylic acid esterification under a particular set of conditions can readily be determined by the skilled artisan without undue experimentation.

The reaction is simply carried out by adding the desired stoichiometric amount of acrylic or methacrylic acid or derivatives and benzoic acid derivatives plus catalyst to the base epoxy functional organopolysiloxane and heating. The temperature of the reaction should range from 75° C. to about 150° C. for a time period of 0.5 hours to about 24 hours.

Suitable amine functional base polymers may be produced by any of a variety of methods. In Bailey U.S. Pat. No. 2,947,771 aminofunctional silane is equilibrated with polysiloxane in the presence of alkali-metal hydroxide. In Friedman U.S. Pat. No. 3,598,853 an aminofunctional silane is condensed with silanol terminated polydiorganosiloxane. U.S. Pat. Nos. 4,584,393 and 4,565,885 disclose the production of disiloxanes by contacting an acyclic olefinic silazane with a hydrosilation catalyst to form an intermediate which is hydrolyzed. Other methods of preparing siloxanes and polysiloxanes are described in Holdstock, et al. U.S. Pat. No. 3,544,498; Martin U.S. Pat. No. 3,890,269, Jex, et al. U.S. Pat. No. 2,930,809, Jex, et al. U.S. Pat. No. 2,921,950 Jex, et al. U.S. Pat. No. 3,045,036 and Piskoti U.S. Pat. No. 4,633,002. The aminofunctional polysiloxanes described in these references and their methods of preparation are incorporated herein by reference.

A preferred amine functional base silicone polymer has units of the formula:

$$R_i K_j SiO_{(4-i-j)/2} \quad (7)$$

where R is given above, K is amine functional substituted or unsubstituted hydrocarbon of from 1 to about 15 carbon atoms, i is 0, 1 or 2; j is 1, 2 or 3; and i+j=1, 2 or 3. Suitable K radicals include methylamine, propylamine, cyclohexylamine, phenylamine, —CH$_2$CH$_2$CH$_2$NHCH$_2$CH$_2$CH$_2$NH$_2$,
—CH$_2$CH$_2$—O—CH$_2$CH$_2$NHCH$_2$CH$_2$CH$_2$NH$_2$,
—CH$_2$CH$_2$S CH$_2$CH$_2$NH$_2$,
—CH$_2$CH$_2$N(CH$_2$CH$_2$NH$_2$)CH$_2$CH$_2$NH$_2$, etc., For the sake of economy and simplicity K is preferably propyl amine. There should be a sufficient number of units of formula (7) in the base silicone polymer to provide reactive sites for the required acrylic or methacrylic functions and to provide reactive sites for the required benzoyl functions.

The amidization reaction of the amine function to the carboxylic acid and preferably the acid ester or chloride thereof may be carried out with or without an acid catalyst at temperatures ranging from about 50° to 200° C. Depending on conditions, the reaction may be completed in from ½ to 6 hours.

Hydroxy functional base silicones might be produced by the reaction of allyl alcohol with a buffered silicone hydride polymer in the presence of a platinum catalyst. It can be utilized in a similar manner to the base polymers exemplified above.

Acrylic or methacrylic acid and its derivatives suitable for reaction with the base silicone polymers are acrylic or methacrylic acid, acid esters thereof and acid chlorides. Similarly, benzoic acid and its derivatives include the benzoic acid esters, acid chlorides as well as the substituted benzoic acids.

The radiation curable silicone polymer described herein must be stored out of light sources which would reduce its shelf life. Otherwise, it may be utilized as acrylic functional silicones have heretofore been employed. They can be formulated alone to self cure. They may be formulated with organic acrylic groups to coreact therewith. Further, they may be formulated with mercapto silicones to crosslink or cure with those materials. Reactive or non-reactive non-silicone diluents may be added as convenient to the desired use.

Curing may be accomplished by simple exposure to sufficient UV radiation, augmented by final cure at room temperature or elevated temperature. Cure promoters, i.e. amine-benzophenone combinations, can be employed to overcome oxygen inhibition. Of course a combination of UV radiation and exposure to elevated temperatures will produce the most rapid cure.

In order that those skilled in the art might be better able to practice the present invention, the following examples are provided by way of illustration and not by way of limitation. All parts are in parts by weight.

EXAMPLE 1

350 grams of a 65 cps, epoxy-functional fluid with 1.4245 refractive index prepared by addition of vinylcyclohexeneoxide to an SiH-fluid was dispersed in 200 grams of toluene. 0.5 moles of cyclohexylepoxide function were present in this solution. 37 grams of benzoic acid (0.3 mole) were added, and this mixture refluxed at 120° C. for 16 hours. Titration revealed that 95% of the benzoic acid had reacted with the oxirane groups at this point. 25 grams of acrylic acid (0.35 mole)+0.2 gram phenothiazine were then added, followed by 124 ° C. reflux for 23 hours, resulting in reaction of 0.15 mole acrylic acid. The reaction mixture was then stripped to 150° C., at 200 MM vacuum plus nitrogen sweep, providing 390 grams yield of a 7900 cps. fluid, N$_2^D$=1.4435. The structure of this polymer can be represented as:

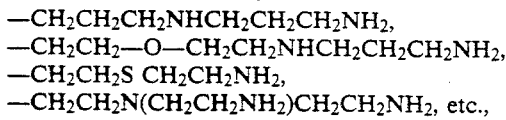

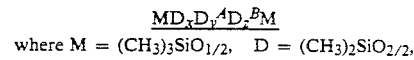

where M = (CH$_3$)$_3$SiO$_{1/2}$, D = (CH$_3$)$_2$SiO$_{2/2}$,

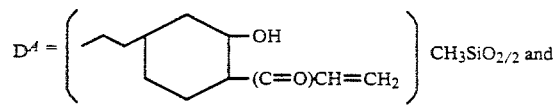

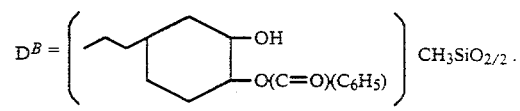

EXAMPLES 2-7

The radiation curable silicone polymer of Example 1 was tested by applying 1 mil thick coatings of the formulations of Table 1 to super calendared Kraft paper and then exposing to medium-pressure mercury vapor UV light sources. Cure quality was assessed per standard paper release techniques; smear, migration and anchorage. In Table 1, diethoxyacetophenone is DEA, a photocatalyst, and diisopropylaminoethanol is DIPAE, a cure promoter to overcome oxygen inhibition.

TABLE 1

|  | 2 | 3 | 4 | 5 | 6 | 7 |
|---|---|---|---|---|---|---|
| MD$_x$D$_y^A$D$_z^B$M | 10 | 10 | 10 | 10 | 10 | 10 |
| DEA | 0.4 | 0.4 | — | — | — | — |
| DIPAE | — | — | — | — | 0.4 | 0.4 |
| Atmosphere | N$_2$ | Air | N$_2$ | Air | N$_2$ | Air |
| UV dose, mJ/cm$^2$ | 60 | 2500 | 450 | 2500 | 150 | 2500 |
| *Remarks | Cured, ss, nm | NC | Cured, ss, nm | NC | Cured, ns, nm | Cured, ss, nm |

*NC = no cure
ss = slight smear
ns = no smear
nm = no migration

What is claimed is:

1. A method for producing an acrylic or methacrylic functional polysiloxane, self-sensitized to UV radiation, comprising the steps of:
   (a) reacting in the absence of UV radiation a base polysiloxane having functional groups reactive with acid chlorides, carboxylic acids or carboxylic acid esters with acrylic or methacrylic acid or derivatives and benzoic acid, substituted benzoic acid, or derivatives, and
   (b) recovering said acrylic or methacrylic functional polysiloxane.

2. The method of claim 1 wherein said base polysiloxane is epoxy functional base silicone polymer.

3. The method of claim 2 wherein said epoxy functional base silicone polymer has units of the formula:

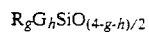

where R is hydrogen or a C$_{(1-8)}$ substituted or unsubstituted hydrocarbon; G is epoxy-functional substituted or unsubstituted hydrocarbon of from 3 to about 15 carbon atoms; 9 is 0, 1 or 2; h is 1, 2 or 3; and g+h is 1, 2 or 3.

4. The method of claim 2 wherein said step of reacting is carried out with a tetraalkylurea or tetraalkylguanidine at a temperature of about 75° to about 150° C. for a time of about 0.5 to about 24 hours.

5. The method of claim 2 wherein said acrylic or methacrylic acid or derivatives is acrylic or methacrylic acid or acrylic or methacrylic acid ester.

6. The method of claim 2 wherein said benzoic acid substituted benzoic acid or derivatives are benzoic acid, benzoic acid ester, substituted benzoic acid or substituted benzoic acid ester.

7. The method of claim 2 wherein said epoxy functional base silicone polymer is cycloaliphatic epoxy functional.

8. The method of claim 1 wherein said base polysiloxane is amine functional base silicone polymer.

9. The method of claim 8 wherein said amine functional base silicone polymer has units of the formula:

$$R_i K_j SiO_{(4-i-j)/2}$$

where R is hydrogen or a $C_{(1-8)}$ substituted or unsubstituted hydrocarbon, K is an amine functional substituted or unsubstituted hydrocarbon of from 1 to about 15 carbon atoms; i is 0, 1 or 2; j is 1, 2 or 3; and i+j=1, 2 or 3.

10. The method of claim 8 wherein said step of reacting is carried out with an acid catalyst at temperatures of from about 50° to 200° C. and for a time of about ½ to 6 hours.

11. The method of claim 8 wherein said acrylic or methacrylic acid or derivatives are acrylic or methacrylic acid ester or acrylic or methacrylic acid chloride.

12. The method of claim 8 wherein said benzoic acid, substituted benzoic acid, or derivatives, are benzoic acid ester, substituted benzoic acid ester, benzoic acid chloride, or substituted benzoic acid chloride.

13. The method of claim 8 wherein said amine functional base silicone polymer is methylamine, propylamine, cyclohexylamine, phenylamine, —CH$_2$CH$_2$CH$_2$NHCH$_2$CH$_2$NH$_2$, —CH$_2$CH$_2$—O—CH$_2$CH$_2$NHCH$_2$CH$_2$CH$_2$NH$_2$ —CH$_2$CH$_2$SCH$_2$CH$_2$NH$_2$, or —CH$_2$CH$_2$N(CH$_2$CH$_2$NH$_2$)CH$_2$CH$_2$NH$_2$ functional.

* * * * *